United States Patent [19]
Ohtaki et al.

[11] Patent Number: 5,843,478
[45] Date of Patent: Dec. 1, 1998

[54] LANPERISONE FORMULATION

[75] Inventors: Hiroshi Ohtaki, Koga; Rie Joshita, Tokyo, both of Japan

[73] Assignee: Nippon Kayaku Kabushiki Kaisha, Tokyo, Japan

[21] Appl. No.: 721,552

[22] Filed: Sep. 26, 1996

[30] Foreign Application Priority Data

Oct. 6, 1995 [JP] Japan ................................. 7-284342

[51] Int. Cl.$^6$ .............................. A61K 9/26; A61K 9/50
[52] U.S. Cl. ........................................... 424/470; 424/499
[58] Field of Search .................................. 424/468, 470, 424/499; 514/427

[56] References Cited

FOREIGN PATENT DOCUMENTS

| 0 105 632 | 4/1984 | European Pat. Off. . |
| 0 200 942 | 11/1986 | European Pat. Off. . |
| 0266577B1 | 10/1987 | European Pat. Off. . |
| 0 266 577 | 5/1988 | European Pat. Off. . |

OTHER PUBLICATIONS

Database WPI, Section Ch, Week 9334, Derwent Publications Ltd., London, GB; Class B03, AN 93–269751 XP002020977 & JP–A–05 186 345 (Nippon Kayaku KK), 27 Jul. 1993 *abstract*.

Pharm Tech Japan vol. 7, No. 11 (1991) pp. 91(1311)–98(1318) and a partial English translation.

*Primary Examiner*—Thurman K. Page
*Assistant Examiner*—Sharon Howard
*Attorney, Agent, or Firm*—Nields, Lemack & Dingman

[57] ABSTRACT

A lanperisone hydrochloride compression-molded formulation comprising the first granules containing lanperisone hydrochloride and the second granules containing substantially no lanperisone hydrochloride but at least one pharmaceutical additive(s) selected from the group consisting of sugars, crystalline celluloses and cellulose derivatives is an excellent formulation which has a high storage stability because the decomposition of lanperisone hydrochloride is suppressed.

15 Claims, No Drawings

LANPERISONE FORMULATION

BACKGROUND OF THE INVENTION

1. Field of the Invention

The present invention relates to a pharmaceutical formulation with a good storage stability of lanperisone hydrochloride having a central muscle-relaxing effect and the like.

2. Disclosure of the Related Art (R)-(−)-2-Methyl-3-pyrrolidino-1-(4-trifluoromethylphenyl)-1-propanone hydrochloride (hereinafter referred to as "lanperisone hydrochloride") is used as an active ingredient in the pharmaceutical formulation of the present invention.

It is known that lanperisone hydrochloride has a central muscle-relaxing effect and is effective in preventing or curing temporomandibular arthrosis (Japanese Patent Unexamined Publication Nos. 1-131171 and 5-186345 and EP-A-266577).

The present inventors found that conventional tablets of lanperisone hydrochloride are very disadvantageous in practice, for example, as follows: lanperisone hydrochloride is so unstable in the tablets that it is easily converted into an optical isomer ((+)-form), olefin form or pyrrolidine hydrochloride; and the tablets are insufficient in hardness. Therefore, an object of the present invention is to provide a practical lanperisone hydrochloride formulation free from such disadvantages.

SUMMARY OF THE INVENTION

The present inventors conducted various researches and consequently found that compression mold of the mixture of the specific two kinds of granules described below gives a formulation markedly improved in the above-mentioned defects, and that when specific pharmaceutical additives are used together with lanperisone hydrochloride, a fairly improved compression-molded formulation can be obtained without use of the said two kinds of granules. Thus, the present invention has been accomplished.

An object of the present invention is to provide a lanperisone hydrochloride compression-molded formulation (1) comprising (i) the first granules containing lanperisone hydrochloride, and (ii) the second granules containing substantially no lanperisone hydrochloride but at least one medicinal additive(s).

Another object of the present invention is to provide a formulation (2), the above-mentioned formulation (1) which has a tensile strength of at least 10 kg/cm².

Further another object of the present invention is to provide a formulation (3), the above-mentioned formulation (1) wherein the contents of lanperisone hydrochloride and its optical isomer after storage of the formulation at 65° C. for 7 days are 90 wt % or more and 3 wt % or less, respectively, based on the sum of the following weights (a) and (b):

(a) the total weight of lanperisone hydrochloride and its optical isomer contained in the formulation after the storage, and (b) the weight of decomposed-lanperisone hydrochloride calculated from the weight of pyrrolidine hydrochloride, which is formed by decomposition of lanperisone hydrochloride, contained in the formulation after the storage.

Still another object of the present invention is to provide a formulation (4), the above-mentioned formulation (1) wherein the first granules comprise lanperisone hydrochloride and at least one pharmaceutical additive which is such that when lanperisone hydrochloride and the pharmaceutical additive(s) are blended in the weight ratio of 1:1, compression-molded and then stored at 65° C. for 3 days, the residual lanperisone hydrochloride content after the storage is 50 wt % or more based on the weight of the lanperisone hydrochloride blended.

Still another object of the present invention is to provide a formulation (5), the above-mentioned the formulation (2) wherein a time required for dissolution of 75 wt % of lanperisone hydrochloride in the whole formulation is 5 minutes or less in water.

Still another object of the present invention is to provide a formulation (6), the above-mentioned formulation (2) wherein one or more of the pharmaceutical additive(s) are selected from the group consisting of sugars, crystalline celluloses and cellulose derivatives.

Still another object of the present invention is to provide a formulation (7), the above-mentioned formulation (2) or (3) which comprises (i) the first granules comprising lanperisone hydrochloride and a cellulose derivative as essential constituents, and (ii) the second granules comprising a crystalline cellulose as an essential constituent, and further said the first granules or said the second granules, or both containing a sugar.

Still another object of the present invention is to provide a formulation (8), the above-mentioned formulation (7) wherein the proportion of lanperisone hydrochloride in the first granules is at least 60 wt % based on the total weight of lanperisone hydrochloride and the cellulose derivative in the first granules, and is 20 to 90 wt % based on the weight of the whole formulation.

Still another object of the present invention is to provide a formulation (9), the above-mentioned formulation (7) which has the following composition wherein proportions relative to the whole formulation are:

| | |
|---|---|
| lanperisone hydrochloride | 10 to 86 wt % |
| sugar | 10 to 85 wt % |
| crystalline cellulose | 2 to 30 wt % |
| cellulose derivative | 2 to 25 wt %. |

Still another object of the present invention is to provide a formulation (10), the above-mentioned formulation (7) which has the following composition wherein proportions relative to the whole formulation are:

| | |
|---|---|
| lanperisone hydrochloride | 20 to 60 wt % |
| sugar | 20 to 60 wt % |
| crystalline cellulose | 5 to 25 wt % |
| cellulose derivative | 5 to 20 wt %. |

Still another object of the present invention is to provide a formulation (11), the above-mentioned formulation (3) wherein the proportion of lanperisone hydrochloride in the first granules is at least 70 wt % based on the weight of the whole first granules and is 30 to 60 wt % based on the weight of the whole formulation, and the proportion of crystalline cellulose in the second granules is at least 20 wt % based on the weight of the whole second granules and is 5 to 25 wt % based on the weight of the whole formulation, the balance being of (A) at least one member selected from the group consisting of sugars and cellulose derivatives and (B) optionally other pharmaceutical additive(s).

Still another object of the present invention is to provide a lanperisone hydrochloride compression-molded formulation (12) which comprises lanperisone hydrochloride, a sugar, a crystalline cellulose and a cellulose derivative as essential constituents and satisfies the following conditions: the formulation has a tensile strength of at least 10 kg/cm$^2$, and the contents of lanperisone hydrochloride and its optical isomer after storage of the formulation at 65° C. for 7 days are 90 wt % or more and 3 wt % or less, respectively, based on the sum of the following weights (a) and (b):

(a) the total weight of lanperisone hydrochloride and its optical isomer contained in the formulation after the storage, and (b) the weight of decomposed-lanperisone hydrochloride calculated from the weight of pyrrolidine hydrochloride, which is formed by decomposition of lanperisone hydrochloride, contained in the formulation after the storage.

Still another object of the present invention is to provide a formulation (13), the above-mentioned formulation (12) wherein the proportions of lanperisone hydrochloride, the sugar, the crystalline cellulose and the cellulose derivative are 30 to 60 wt %, 20 to 60 wt %, 5 to 25 wt % and 5 to 20 wt %, respectively, based on the weight of the whole formulation.

Still another object of the present invention is to provide a formulation (14), any of the above-mentioned formulations (7), (9), (11) and (12) wherein the sugar is a monosaccharide or an oligosaccharide.

BRIEF DESCRIPTION OF THE PREFERRED EMBODIMENTS

The present invention is explained below in detail.

Although the first granules containing lanperisone hydrochloride may be composed of only lanperisone hydrochloride, they are usually preferably composed of lanperisone hydrochloride, a binder and optionally other pharmaceutical additive(s) such as an excipient.

The second granules containing substantially no lanperisone hydrochloride but at least one pharmaceutical additive(s) usually comprise pharmaceutical additive(s) such as an excipient and a binder. However, the second glanules may contain lanperisone hydrochloride in such an amount that the effect of the present invention is not substantially lessened.

As the compression-molded formulation, there may be exemplified tablets usually obtained by compression molding with a tableting machine or the like.

The total content of lanperisone hydrochloride and its optical isomer or the content of only the optical isomer in the present invention can be quantitatively determined according to a liquid chromatography on a column for measuring the total content or a column for optical resolution, respectively. Examples of packings which may be use for the columns are as follows:

Column for liquid chromatography for measuring the total content

Packing: 5 μm octylsilylated silica gel;

Column: 4 mmφ, 20 cm (made of stainless steel).

Column for liquid chromatography for optical resolution

Packing: 5 μm N-(R)-1-(α-naphthyl)ethylaminocarbonyl-(S)-valylaminopropylsilylated silica gel;

Column: 4 mmφ, 25 cm (made of stainless steel).

The amount of pyrrolidine hydrochloride can be quantitatively determined according to spectrophotometry measuring absorbance at a wavelength of 435 nm.

The term "weight of decomposed-lanperisone hydrochloride calculated from the weight of pyrrolidine hydrochloride" used herein means a value (mg) calculated by multiplying the amount (mg) of pyrrolidone hydrochloride by the molecular weight ratio of lanperisone hydrochloride to pyrrolidone hydrochloride.

Although the pharmaceutical additive(s) used in the present invention is not particularly limited, preferable examples thereof are excipients, disintegrators, binders and additives having two or more of such functions. Specific examples of the pharmaceutical additive(s) are sugars, crystalline celluloses and cellulose derivatives. These may be used singly or in combination therewith.

The sugars are usually used as excipients and include, for example, monosaccharides, oligosaccharides, polysaccharides and sugar alcohols. Specific examples of the monosaccharides are glucose and fructose. The oligosaccharides usually refer to sugars composed of about 2 to about 6 simple sugar units bound together, and preferable examples thereof are lactose, sucrose and maltose and the like. The polysaccharides refer to sugars composed of simple sugar units bound together in a number larger than that in the oligosaccharides, and typical examples thereof are corn starch and hydroxypropyl starch and the like. The sugar alcohols include mannitol, xylitol, sorbitol, and the like. Of these sugars, the monosaccharides and the oligosaccharides are preferable because of their little undesirable influence on lanperisone hydrochloride.

As the cellulose derivatives, there may be exemplified cellulose ethers obtained by etherifying hydroxyl groups of cellulose. Although the molecular weight of an ether group in each case may not be unequivocally determined because it is varied depending on purpose of use, it is usually preferably 200 or less, more preferably 150 or less. As such a group, substituted or unsubstituted lower alkyl groups may be exemplified. Their substituents include, for example, hydroxyl group, carboxyl group and amino group. Specific examples of the cellulose derivatives are water-soluble cellulose derivatives such as hydroxypropyl cellulose (HPC), methyl cellulose and hydroxypropylmethyl cellulose which are used as binders and the like; and water-swellable cellulose derivatives such as carboxymethyl cellulose (hereinafter referred to as "carmelose") which are used as excipients, disintegrators and the like. The water-soluble cellulose derivatives are usually such that the viscosity of a 2% aqueous solution of the derivative is preferably 4,000 cps or less, more preferably 50 cps or less, at 20° C.

As pharmaceutical additives other than the above-exemplified additives, there may be exemplified lubricants, corrigent and coloring agents.

The lubricants include, for example, magnesium stearate, stearic acid and talc. The corrigent include, for example, artificial sweeteners (e.g. saccharin sodium and Aspartame), acidulants (e.g. citric acid, malic acid and tartaric acid) and flavoring materials (e.g. menthol, lemon flavor and orange flavor). The coloring agents include, for example, food coloring agents such as food Yellow No. 5.

When any of the pharmaceutical additives is used in a large proportion (for example, 10 wt % or more) relative to the whole formulation, it is preferably one which has less undesirable influence on lanperisone hydrochloride. A test for selecting such a preferable pharmaceutical additive (hereinafter referred to as "pharmaceutical additive selective test") can be carried out by blending lanperisone hydrochloride and a pharmaceutical additive in the weight ratio of 1:1, mixing them uniformly, compression-molding the resulting mixture, and storing the thus obtained tablets at 65° C. for 3 days. There is preferably used a pharmaceutical additive which is such that the lanperisone hydrochloride content after the storage is high. This lanperisone hydrochloride content is preferably 50 wt % or more, more preferably 60 wt % or more, most preferably 70 wt % or more, based on the initial weight of lanperisone hydrochloride blended.

Specific examples of the preferable additive are monosaccharides such as glucose; oligosaccharides such as lactose and sucrose; sugar alcohols such as mannitol; polysaccharides such as corn starch and hydroxypropyl starch (HPS); water-swellable cellulose derivatives such as carmelose and its salts; and crystalline celluloses. As these additives, commercially available ones may be used. For example, the crystalline celluloses include Avicel® PH101 (mfd. by Asahi Chemical Industry Co.). The carmelose includes NS300 (Trade name, Gotoku Chemical Co., Ltd.). HPS includes HPC-L (mfd. by Nippon Soda Co., Ltd.).

Particularly in the case of the formulation of the present invention comprising the two kinds of granules, when an excipient or a disintegrator or both is incorporated into the first granules in a proportion of 10 wt % or more based on the weight of lanperisone hydrochloride, the excipient or the disintegrator or both is such that the lanperisone hydrochloride content after the storage is preferably 90 wt % or more, more preferably 95 wt % or more, in the above-mentioned pharmaceutical additive selective test. As such an excipient or disintegrator, there may be exemplified water-swellable starch derivatives such as hydroxypropyl starch (HPS), and water-swellable cellulose derivatives such as carmelose and its salts. Of carmelose and its salts, carmelose is preferable.

The amount of a binder incorporated into the first granules is small but it is considered that the binder has a relatively large influence on lanperisone hydrochloride. Therefore, the binder is preferably one which satisfies the following requirement: when lanperisone hydrochloride and the binder are blended in the weight ratio of 10:1, uniformly mixed, compression-molded, and stored at 65° C. for 3 days, the lanperisone hydrochloride content after the storage is 95 wt % or more of the initial content of lanperisone hydrochloride blended, and is preferably substantially not less than the initial content.

As such a preferable binder, there may be exemplified water-soluble cellulose derivatives such as hydroxypropyl cellulose (HPC), methyl cellulose (MC) and hydroxypropylmethyl cellulose (HPMC).

Usually, the formulation of the present invention may be produced by preparing the two kinds of granules and then compression-molding the granules. The pharmaceutical additive(s) may be previously incorporated into the granules, or they may be blended with the granules before the compression molding.

A method for preparing the granules in the present invention is not particularly limited. The granules may be prepared, for example, by mixing the components uniformly and granulating the resulting mixture according to a conventional technique such as fluidized-bed granulation or crushing granulation.

The formulation of the present invention may be produced by mixing the above-mentioned granules and optionally other pharmaceutical additives thoroughly, and compression-molding the resulting mixture by tableting or the like by a conventional method.

A process for producing the formulation comprising the two kinds of granules of the present invention is more specifically explained below.

The first granules may be obtained usually as followed: lanperisone hydrochloride or a mixture of lanperisone hydrochloride and a pharmaceutical excipient or disintegrator is sprayed with a binder solution and subjected to fluidized-bed granulation, or a mixture of lanperisone hydrochloride, a binder solution and optionally a pharmaceutical excipient and the like is granulated by crushing or the like, and the granules thus obtained are dried. Usually, the amount of the binder is approximately 0.5–5 wt %, preferably approximately 1–4 wt %, based on the weight of the whole first granules. The lanperisone hydrochloride content of the first granules is preferably high. It is usually 40 wt % or more, preferably 60 wt % or more, more preferably 70 wt % or more. The upper limit of the lanperisone hydrochloride content is preferably 99.5 wt % or less. The balance is of pharmaceutical additives such as other pharmaceutical excipients which are added if necessary.

The second granules may be obtained usually as followed: an excipient is sprayed with a binder solution and subjected to fluidized-bed granulation, or a mixture of an excipient and a binder solution is granulated by crushing or the like, and the granules thus obtained are dried. The amount of the binder incorporated into the second granules is usually 0.1–7 wt %, preferably approximately 0.2–5 wt %, based on the whole second granules.

The thus prepared first granules and the second granules and optionally pharmaceutical additives such as a lubricant are mixed in a twin-shell blender or the like to obtain mixed granules for compression molding. The mixing proportions of the first granules and the second granules may be properly adjusted depending on the lanperisone hydrochloride content of a desired final formulation.

The tensile strength of the formulation of the present invention is preferably at least 10 kg/cm$^2$, more preferably 12 kg/cm$^2$ or more. Although varied depending on the composition and size of the formulation, the compression pressure at the compression molding is approximately 1,000–2,000 kg/cm$^2$.

The tensile strength is a value indicating the essential strength independent of the size of a test specimen and is calculated from compression breaking load by the following equation:

$$\sigma t = \frac{2P}{\pi D l} \times 100$$

wherein

σt: tensile strength (kg/cm$^2$)

P: compression breaking load (t)

D: diameter of the specimen (cm)

l: length of test specimen (cm)

The formulation of the present invention obtained in the manner described above is excellent in storage stability. After the formulation is stored at 65° C. for 7 days, its lanperisone hydrochloride content is preferably 90 wt % or more, more preferably 95 wt % or more, based on the sum of the following weights (a) and (b), and its lanperisone hydrochloride optical isomer content is preferably 3 wt % or less, more preferably 1.5 wt % or less, based on the sum of the following weights (a) and (b):

(a) the total weight of lanperisone hydrochloride and its optical isomer contained in the formulation after the storage, and (b) the weight of decomposed-lanperisone hydrochloride calculated from the weight of the pyrrolidine hydrochloride, which is formed by decomposition of lanperisone hydrochloride, contained in the formulation after the storage.

From the results of preliminary experiments carried out by the present inventors, it is considered that a time required for dissolution of 75 wt % of lanperisone hydrochloride in the whole formulation is preferably 5 minutes or less, more preferably 4 minutes or less, most preferably 3 minutes and or less, in water, for improving the bioavailability of lanperisone hydrochloride.

A dissolution test is carried out according to the dissolution test method No. 2 of the general test method prescribed in the Japanese Pharmacopoeia by using purified water as a test liquid, and stirred at 100 rpm.

Next, there is explained below a preferable composition of the formulation of the present invention which is employed when the formulation comprises the two kinds of granules.

The formulation comprises (i) the first granules comprising lanperisone hydrochloride and a cellulose derivative as essential constituents and (ii) the second granules comprising a crystalline cellulose as an essential constituent, and the first granules or the second granules, or both contain a sugar. In the formulation, the proportion of lanperisone hydrochloride in the first granules is preferably at least 60 wt % based on the total weight of lanperisone hydrochloride and the cellulose derivative in the first granules, and is preferably 20 to 90 wt % based on the weight of the whole formulation.

The blending proportions of components relative to the whole formulation are preferably as follows:

| | |
|---|---|
| lanperisone hydrochloride | 10 to 86 wt % |
| sugar | 10 to 85 wt % |
| crystalline cellulose | 2 to 30 wt % |
| cellulose derivative | 2 to 25 wt %. |

The blending proportions are more preferably as follows:

| | |
|---|---|
| lanperisone hydrochloride | 20 to 60 wt %, preferably 30 to 60 wt % |
| sugar | 20 to 60 wt % |
| crystalline cellulose | 5 to 25 wt % |
| cellulose derivative | 5 to 20 wt %. |

The aforesaid cellulose derivative may contain a water-soluble cellulose derivative as a binder. In this case, the proportion of the water-soluble cellulose derivative is usually 0.3 wt % or more, preferably 0.5 wt % or more, more preferably 0.7 wt % or more and 7 wt % or less, preferably 5 wt % or less, more preferably 3 wt % or less, based on the weight of the whole formulation.

A formulation preferable from the viewpoint of all of the stability of lanperisone hydrochloride, the hardness of tablets and the release of lanperisone hydrochloride from the tablets by dissolution is preferably produced by combining (1) lanperisone hydrochloride, (2) a sugar (preferably corn starch, a monosaccharide or an oligosaccharide), (3) crystalline cellulose, and (4) a cellulose derivative (preferably a water-swellable cellulose derivative such as carmelose).

According to the results of preliminary experiments carried out according to the present inventors, the above-mentioned formulation need not be produced by a granules binary-mixture method, and a preferable compression-molded lanperisone hydrochloride formulation can be obtained also by mixing the above-mentioned four components and optionally other pharmaceutical additives thoroughly, and compression-molding the resulting mixture as it is or after its fluidized-bed granulation to obtain tablets. This process is preferably adopted when the lanperisone hydrochloride content is 30 wt % or more based on the weight of the whole formulation.

The formulation may contain other pharmaceutical additives in addition to the above-mentioned components. In this case, the content of the other pharmaceutical additives is usually 0.01 to 2 wt % based on the weight of the whole formulation, and the proportions of the above-mentioned components are reduced as much.

The present invention is concretely illustrated with the following examples, which should not be construed as limiting the scope of the invention.

EXAMPLE 1

① Lanperisone hydrochloride and NS300 (Trade name, Gotoku Chemical Co., Ltd.) were mixed, sprayed with a HPC-L (mfd. by Nippon Soda Co., Ltd.) solution, and then granulated and dried with a fluidized-bed granulating and drying machine (Model FLO-2, Freund Industrial Co., Ltd.) to obtain first granules.

② Lactose and Avicel® PH101 (mfd. by Asahi Chemical Industry Co.) were mixed, sprayed with a HPC-L solution, and then granulated and dried with a fluidized-bed granulating and drying machine (Model FLO-2, Freund Industrial Co., Ltd.) to obtain the second granules.

③ The first granules, the second granules and magnesium stearate were mixed in a twin-shell blender (Model II, Tutui Rikagaku Kikai Co., Ltd.) to obtain granules for tableting.

④ The granules for tableting were compression-molded into tablets with a single-punch tablet machine (Model KT-2, Okada Seiko Co., Ltd.).

⑤ The tablets were subjected to PTP packaging to obtain samples.

The compositions employed in Example 1 are shown in Table 1.

TABLE 1

| | Material | Proportion (%) |
|---|---|---|
| The first granules | Lanperisone hydrochloride | 25 |
| | NS300 | 10 |
| | HPC-L | 1 |
| The second granules | Lactose | 43 |
| | Avicel ® PH101 | 20 |
| | HPC-L | 0.5 |
| Lubricant | Magnesium stearate | 0.5 |

EXAMPLE 2

① Lanperisone hydrochloride, NS300 and lactose were mixed, sprayed with a HPC-L solution, and then granulated and dried with a fluidized-bed granulating and drying machine (Model FLO-2, Freund Industrial Co., Ltd.) to obtain the first granules.

② Avicels PH101 was sprayed with a HPC-L solution and granulated and dried with a fluidized-bed granulating and drying machine (Model FLO-2, Freund Industrial Co., Ltd.) to obtain the second granules.

③ The first granules, the second granules and magnesium stearate were mixed in a twin-shell blender (Model II, Tutui Rikagaku Kikai Co., Ltd.) to obtain granules for tableting.

④ The granules for tableting were compression-molded into tablets with a single-punch tablet machine (Model KT-2, Okada Seiko Co., Ltd.).

⑤ The tablets were subjected to PTP packaging to obtain samples.

The compositions employed in Example 2 are shown in Table 2.

TABLE 2

|  | Material | Proportion (%) |
| --- | --- | --- |
| The first granules | Lanperisone hydrochloride | 25 |
|  | NS300 | 10 |
|  | HPC-L | 1 |
|  | Lactose | 43 |
| The second granules | Avicel ® PH101 | 20 |
|  | HPC-L | 0.5 |
| Lubricant | Magnesium stearate | 0.5 |

EXAMPLE 3

① Lanperisone hydrochloride and NS300 were mixed, sprayed with a HPC-L solution, and then granulated and dried with a fluidized-bed granulating and drying machine (Model FLO-2, Freund Industrial Co., Ltd.) to obtain the first granules.

② Lactose and Avicel® PH101 were mixed, sprayed with a HPC-L solution, and then granulated and dried with a fluidized-bed granulating and drying machine (Model FLO-2, Freund Industrial Co., Ltd.) to obtain the second granules.

③ The first granules, the second granules and magnesium stearate were mixed in a twin-shell blender (Model II, Tutui Rikagaku Kikai Co., Ltd.) to obtain granules for tableting.

④ The granules for tableting were compression-molded into tablets with a single-punch tablet machine (Model KT-2, Okada Seiko Co., Ltd.).

⑤ The tablets were subjected to PTP packaging to obtain samples.

The compositions employed in Example 3 are shown in Table 3.

TABLE 3

|  | Material | Proportion (%) |
| --- | --- | --- |
| The first granules | Lanperisone hydrochloride | 40 |
|  | NS300 | 8 |
|  | HPC-L | 1 |
| The second granules | Lactose | 30 |
|  | Avicel ® PH101 | 20 |
|  | HPC-L | 0.5 |
| Lubricant | Magnesium stearate | 0.5 |

EXAMPLE 4

① Lanperisone hydrochloride was sprayed with a HPC-L solution and granulated and dried with a fluidized-bed granulating and drying machine (Model FLO-2, Freund Industrial Co., Ltd.) to obtain the first granules.

② Lactose, NS300 and Avicel® PH101 were mixed, sprayed with a HPC-L solution, and then granulated and dried with a fluidized-bed granulating and drying machine (Model FLO-2, Freund Industrial Co., Ltd.) to obtain the second granules.

③ The first granules, the second granules and magnesium stearate were mixed in a twin-shell blender (Model II, Tutui Rikagaku Kikai Co., Ltd.) to obtain granules for tableting.

④ The granules for tableting were compression-molded into tablets with a single-punch tablet machine (Model KT-2, Okada Seiko Co., Ltd.).

⑤ The tablets were subjected to PTP packaging to obtain samples.

The compositions employed in Example 4 are shown in Table 4.

TABLE 4

| Compositions in Example 4 | | |
| --- | --- | --- |
|  | Material | Proportion (%) |
| The first granules | Lanperisone hydrochloride | 45 |
|  | HPC-L | 1 |
| The second granules | Lactose | 31 |
|  | NS300 | 10 |
|  | Avicel ® PH101 | 12 |
|  | HPC-L | 0.5 |
| Lubricant | Magnesium stearate | 0.5 |

EXAMPLE 5

① Lanperisone hydrochloride and NS300 (Trade name, Gotoku Chemical Co., Ltd.) were mixed, sprayed with a HPC-L (mfd. by Nippon Soda Co., Ltd.) solution, and then granulated and dried with a fluidized-bed granulating and drying machine (Model FLO-2, Freund Industrial Co., Ltd.) to obtain the first granules.

② Lactose and Avicel® PH101 (mfd. by Asahi. Chemical Industry Co.) were mixed, sprayed with a HPC-L solution, and then granulated and dried with a fluidized-bed granulating and drying machine (Model FLO-2, Freund Industrial Co., Ltd.) to obtain the second granules.

③ The first granules, the second granules and magnesium stearate were mixed in a twin-shell blender (Model II, Tutui Rikagaku Kikai Co., Ltd.) to obtain granules for tableting.

④ The granules for tableting were compression-molded into tablets with a single-punch tablet machine (Model KT-2, Okada Seiko Co., Ltd.).

⑤ The tablets were used as samples.

The compositions employed in Example 5 are shown in Table 5.

TABLE 5

| Compositions in Example 5 | | |
| --- | --- | --- |
|  | Material | Proportion (%) |
| The first granules | Lanperisone hydrochloride | 25 |
|  | NS300 | 10 |
|  | HPC-L | 1 |
| The second granules | Lactose | 43 |
|  | Avicel ® PH101 | 20 |
|  | HPC-L | 0.5 |
| Lubricant | Magnesium stearate | 0.5 |

EXAMPLE 6

① Lanperisone hydrochloride, NS300 and lactose were mixed, sprayed with a HPC-L solution, and then granulated and dried with a fluidized-bed granulating and drying machine (Model FLO-2, Freund Industrial Co., Ltd.) to obtain the first granules.

② Lactose and Avicel® PH101 were mixed, sprayed with a HPC-L solution, and then granulated and dried with a fluidized-bed granulating and drying machine (Model FLO-2, Freund Industrial Co., Ltd.) to obtain the second granules.

③ The first granules, the second granules and magnesium stearate were mixed in a twin-shell blender (Model II, Tutui Rikagaku Kikai Co., Ltd.) to obtain granules for tableting.

④ The granules for tableting were compression-molded into tablets with a single-punch tablet machine (Model KT-2, Okada Seiko Co., Ltd.).

⑤ The tablets were subjected to PTP packaging to obtain samples.

The compositions employed in Example 6 are shown in Table 6.

TABLE 6

Compositions in Example 6

| | Material | Proportion (%) |
|---|---|---|
| The first granules | Lanperisone hydrochloride | 25 |
| | NS300 | 10 |
| | Lactose | 21.5 |
| | HPC-L | 1 |
| The second granules | Lactose | 21.5 |
| | Avicel ® PH101 | 20 |
| | HPC-L | 0.5 |
| Lubricant | Magnesium stearate | 0.5 |

The effects of the present inventions are specifically shown with the following test examples.

TEST EXAMPLE 1

Storage stability—(1)

1. Samples

The formulations obtained in Examples 1 to 4.

2. Test method and test results

Each sample was stored at 40° C. and 75% RH for 4 months, followed by quantitatively determining ① the proportion of the optical isomer, ② the pyrrolidine hydrochloride content and ③ the lanperisone hydrochloride content in the formulation after the storage. Methods for the quantitative determination and expression of these items are as follows.

① Proportion of the optical isomer

Optical resolution into lanperisone hydrochloride and its optical isomer was carried out by a liquid chromatography for optical resolution (HPLC-I), and the area of each single peak of lanperisone hydrochloride and the optical isomer was respectively measured. The proportion of the optical isomer was expressed in terms of the proportion (%) of the peak area of the optical isomer relative to sum of the each peak area of lanperisone hydrochloride and the optical isomer.

② Pyrrolidine hydrochloride content

The amount (mg) of pyrrolidine hydrochloride was quantitatively determined by absorptiometry and expressed in terms of its proportion relative to the initial amount (mg) of lanperisone hydrochloride blended.

③ Lanperisone hydrochloride content (1) The total amount (mg) of lanperisone hydrochloride and its optical isomer was quantiatively determined by internal standard method by using a liquid chromatography incapable of causing optical resolution (HPLC-II). In this case, no optical resolution into lanperisone hydrochloride and its optical isomer was caused.

(2) The total amount (mg) of lanperisone hydrochloride and its optical isomer determined in (1) above was multiplied by the proportion of lanperisone hydrochloride determined in the same manner as for the above item ①, i.e., the proportion of the optical isomer, to determine lanperisone hydrochloride content (mg) after the storage. This lanperisone hydrochloride content (mg) was expressed in terms of its proportion (%) relative to the initial amount (mg) of lanperisone hydrochloride blended.

That is, the lanperisone hydrochloride content (%) was calculated by the following equation:

$$\text{Lanperisone hydrochloride content (\%)} = \frac{\text{(Total amount of lanperisone hydrochloride and its optical isomer) (mg)}}{\text{(Initial amount of lanperisone hydrochloride blended) (mg)}} \times \text{Proportion of lanperisone hydrochloride} \times 100$$

The initial amount (mg) of lanperisone hydrochloride blended in each of the formulations obtained in Examples 1 to 4 was 25 mg, 25 mg, 50 mg or 75 mg, respectively.

The results obtained are shown in Table 7.

In this specification, the term "initial amount of lanperisone hydrochloride blended" means theoretical content of lanperisone hydrochloride in the formulation calculated from the ratio of lanperisone hydrochloride blended for the formulation.

TABLE 7

| Sample | Proportion of optical isomer | Pyrrolidine hydrochloride content | Lanperisone hydrochloride content |
|---|---|---|---|
| Example 1 | 0.8% | 0.53% | 99.2% |
| Example 2 | 0.5% | 0.69% | 97.8% |
| Example 3 | 0.4% | 0.22% | 99.8% |
| Example 4 | 0.1% | 0.29% | 99.2% |

TEST EXAMPLE 2

Storage stability—(2)

1. Sample

The formulation obtained in Example 5.

2. Test method and test results

The sample was stored at 65° C. for 1 week, followed by determining ① the optical isomer content, ② the pyrrolidine hydrochloride content and ③ the lanperisone hydrochloride content in the formulation after the storage. Methods for the determination and expression of these items are as follows.

① Optical isomer content (1) Optical resolution into lanperisone hydrochloride and its optical isomer was carried out by a liquid chromatography for optical resolution (HPLC-I), and the area of each single peak of lanperisone hydrochloride and the optical isomer was respectively measured. There were calculated the proportions of the peak area of the optical isomer and that of lanperisone hydrochloride relative to sum of the each peak area of lanperisone hydrochloride and the optical isomer.

(2) Then, the total amount (mg) determined in ③, (1) below was multiplied by the proportion of the peak area of the optical isomer calculated in (1) above, to obtain a calculated value (mg) of the optical isomer content.

(3) The calculated value (mg) obtained in (2) above was expressed in terms of its proportion (%) relative to the apparent charging amount (the sum [a]+[b] described in the postscript in ③, (3) below).

③ Pyrrolidine hydrochloride content (1) The amount (mg) of pyrrolidine hydrochloride was determined by absorptiometry.

(2) This determined amount was expressed in terms of its proportion relative to the apparent charging amount (the sum [a]+[b] described in the postscript in ③, (3) below).

③ Lanperisone hydrochloride content (1) The total amount (mg) of lanperisone hydrochloride and its optical isomer was determined by internal standard method by using a liquid chromatography incapable of causing optical resolution (HPLC-II).

(2) The total amount (mg) determined in (1) above was multiplied by the proportion of the peak area of lanperisone hydrochloride calculated in ①, (1) above, to obtain a calculated value (mg) of the objective lanperisone hydrochloride content.

(3) The calculated value (mg) obtained in (2) above was expressed in terms of its proportion (%) relative to the apparent charging amount (the sum [a]+[b] described below).

The term "apparent charging amount" means the sum of the following items [a] and [b]:

[a]: the total amount of lanperisone hydrochloride and its optical isomer contained in the formulation after the storage, namely, the amount (mg) determined by the liquid chromatography incapable of causing optical resolution (HPLC-II) in ③, (1) above.

[b]: the amount of lanperisone hydrochloride calculated from the amount of pyrrolidine hydrochloride contained in the formulation after the storage, namely, a value (mg) calculated by multiplying the amount (mg) of pyrrolidine hydrochloride determined in ②, (1) above, by the molecular-weight ratio of lanperisone hydrochloride to pyrrolidine hydrochloride.

The results obtained are shown in Table 8.

TABLE 8

| Lanperisone hydrochloride content | Proportion of optical isomer | Pyrrolidine hydrochloride content |
| --- | --- | --- |
| 96.0% | 0.67% | 1.09% |

TEST EXAMPLE 3

Hardness test

1. Samples
The formulations obtained in Examples 1 to 4.
2. Test method and test results
The compression breaking load of each of the formulations obtained in Examples 1 to 4 is measured with a tablet hardness tester (Model TS-50N, mfd. by Okada Seiko Co., Ltd.), and the tensile strength was calculated by the equation shown above.

The results obtained are shown in Table 9.

TABLE 9

| | Example 1 | Example 2 | Example 3 | Example 4 |
| --- | --- | --- | --- | --- |
| Tensile strength | 11.4 kg/cm$^2$ | 12.6 kg/cm$^2$ | 15.7 kg/cm$^2$ | 12.4 kg/cm$^2$ |

TEST EXAMPLE 4

Dissolution test

1. Samples
The formulations obtained in Examples 1 and 4.
2. Test method and test results
The test was carried out according to the dissolution test method No. 2 of the general test method prescribed in the Japanese Pharmacopoeia by using purified water as a test liquid, and stirred at 100 rpm. The lanperisone hydrochloride concentration of the test liquid was measured by absorptiometry at 2-minute intervals and a time required for 75 wt % dissolution of lanperisone hydrochloride was calculated.

The results obtained are shown in Table 4.

TABLE 10

| | Example 1 | Example 4 |
| --- | --- | --- |
| 75 wt % dissolution time | 1 min. 31 sec. | 2 min. 55 sec. |

From the above results, it is considered that since the formulations of the present invention have a tensile strength of 10 kg/cm$^2$ or more and a 75 wt % dissolution time of lanperisone hydrochloride of 5 minutes or less in water, they are practical and are excellent in lanperisone hydrochloride utilization in a living body.

Furthermore, the formulations of the present invention may be said to be good in storage stability because the remaining rate of lanperisone hydrochloride was maintained at 90% or more and the optical isomer content and the pyrrolidine hydrochloride content after the storage were low.

As is clear from the results described in the above examples and test examples, the present invention makes it possible to obtain a formulation which has a high storage stability because the decomposition of lanperisone hydrochloride is suppressed.

What we claim is:

1. A lanperisone hydrochloride compression-molded formulation comprising
   (i) first granules containing lanperisone hydrochloride, and
   (ii) second granules containing substantially no lanperisone hydrochloride but at least one pharmaceutical additive selected from the group consisting of sugars, crystalline cellulose and cellulose derivatives.

2. A formulation according to claim 1 or 5, which has a tensile strength of at least 10 kg/cm$^2$.

3. A formulation according to claim 1 or 5, wherein the contents of lanperisone hydrochloride and its optical isomer after storage of the formulation at 65° C. for 7 days are 90 wt % or more and 3 wt % or less, respectively, based on the sum of the following weights (a) and (b):
   (a) the total weight of lanperisone hydrochloride and its optical isomer contained in the formulation after said storage, and (b) the weight of decomposed-lanperisone hydrochloride calculated from the weight of pyrrolidine hydrochloride, which is formed by decomposition of lanperisone hydrochloride, contained in the formulation after said storage.

4. A formulation according to claim 1 or 5, wherein a time required for dissolution of 75 wt % of lanperisone hydrochloride in the whole formulation is 5 minutes or less in water.

5. A formulation according to claim 1,
wherein said first granules further contain a cellulose derivative, and
said second granules further contain a crystalline cellulose as an essential constituent,
said first granules or said second granules, or both containing a sugar.

6. A formulation according to claim 5, wherein the proportion of lanperisone hydrochloride in the first granules is at least 60 wt % based on the total weight of lanperisone hydrochloride and the cellulose derivative in the first granules, and is 20 to 90 wt % based on the weight of the whole formulation.

7. A formulation according to claim 5, which has the following composition wherein proportions relative to the whole formulation are indicated:

| | |
|---|---|
| lanperisone hydrochloride | 10 to 86 wt % |
| sugar | 10 to 85 wt % |
| crystalline cellulose | 2 to 30 wt % |
| cellulose derivative | 2 to 25 wt %. |

8. A formulation according to claim 7, which has the following composition wherein proportions relative to the whole formulation are indicated:

| | |
|---|---|
| lanperisone hydrochloride | 20 to 60 wt % |
| sugar | 20 to 60 wt % |
| crystalline cellulose | 5 to 25 wt % |
| cellulose derivative | 5 to 20 wt %. |

9. A formulation according to claim 5, wherein the proportion of lanperisone hydrochloride in the first granules is at least 70 wt % based on the weight of the whole first granules and is 30 to 60 wt % based on the weight of the whole formulation, and the proportion of crystalline cellulose in the second granules is at least 20 wt % based on the weight of the whole second granules and is 5 to 25 wt % based on the weight of the whole formulation, the balance being of (A) at least one member selected from the group consisting of sugars and cellulose derivatives and (B) optionally other pharmaceutical additive(s).

10. A lanperisone hydrochloride compression-molded formulation which comprises lanperisone hydrochloride, a sugar, a crystalline cellulose and a cellulose derivative as essential constituents and satisfies the following conditions: the formulation has a tensile strength of at least 10 kg/cm$^2$, and the contents of lanperisone hydrochloride and its optical isomer after storage of the formulation at 65° C. for 7 days are 90 wt % or more and 3 wt % or less, respectively, based on the sum of the following weights (a) and (b):

(a) the total weight of lanperisone hydrochloride and its optical isomer contained in the formulation after the storage, and (b) the weight of lanperisone hydrochloride calculated from the weight of pyrrolidine hydrochloride contained in the formulation after the storage.

11. A formulation according to claim 10, wherein the proportions of lanperisone hydrochloride, the sugar, the crystalline cellulose and the cellulose derivative are 30 to 60 wt %, 20 to 60 wt %, 5 to 25 wt % and 5 to 20 wt %, respectively, based on the weight of the whole formulation.

12. A formulation according to any one of claims 1, 5, 6, 7, 8, 9, 10 or 11, wherein the sugar is a monosaccharide or an oligosaccharide.

13. A formulation according to claim 2, wherein the sugar is a monosaccharide or an oligosaccharide.

14. A formulation according to claim 3, wherein the sugar is a monosaccharide or an oligosaccharide.

15. A formulation according to claim 4, wherein the sugar is a monosaccharide or an oligosaccharide.

* * * * *